United States Patent [19]
Kenten et al.

[11] Patent Number: 6,048,687
[45] Date of Patent: *Apr. 11, 2000

[54] CYCLING DNA/RNA AMPLIFICATION ELECTROCHEMILUMINESCENT PROBE ASSAY

[75] Inventors: John H. Kenten, Gaithersburg; Rodger Smith, Jefferson, both of Md.

[73] Assignee: IGEN International, Inc., Gaithersburg, Md.

[ * ] Notice: This patent is subject to a terminal disclaimer.

[21] Appl. No.: 08/474,927

[22] Filed: Jun. 7, 1995

Related U.S. Application Data

[63] Continuation of application No. 08/124,686, Sep. 22, 1993, abandoned.

[51] Int. Cl.[7] .............................. C07H 21/04; C12Q 1/68; C12P 19/34
[52] U.S. Cl. .................. 435/6; 435/5; 435/91.1; 435/91.2; 536/24.3; 536/24.33
[58] Field of Search .................. 435/6, 5, 91.2, 435/91.1; 536/24.3–24.33, 26.5

[56] References Cited

U.S. PATENT DOCUMENTS 5,679,519  10/1997  Oprandy ........................................ 435/6

FOREIGN PATENT DOCUMENTS

WO 96/36733  11/1996  WIPO ......................................... 435/6

OTHER PUBLICATIONS

Gemen et al., "A one–tube quantitative HIV–1 RNA NASBA nucleic acid amplification assay using electrochemiluminescence (ECL) labelled probes", Journal of Virological Methods, vol. 49, pp. 157–168, Feb. 14, 1994.

Guatelli, et al. Isothermal, in vitro Amplification of nucleic acids by a multienzyme reaction . . . Proc.Natl.Acad.Sci USA (Mar. 1990) 87:1874–1878.

Fahy et al. Self–Sustained Sequence Replication (3SR): An Isothermal Transcription—Based Amplification . . . PCR Methods and Applications (Aug. 1991) 1:25–33.

Becker–André et al. Absolute mRNA quantification using the polymerase chain reaction (PCR), A Novel . . . Nucl.Acids Res. (1989) 17:9437–9446.

Blackburn et al. Electrochemiluminescence Detection for Development of Immunoassays . . . Clin Chem (1991) 37:1534–1539.

*Primary Examiner*—Stephanie W. Zitomer
*Assistant Examiner*—Arun Chakrabarti
*Attorney, Agent, or Firm*—Whitman Breed Abbott & Morgan LLP

[57] ABSTRACT

This invention relates to an improved process for detecting and quantifying a desired nucleic acid sequence. The process involves synthesizing single stranded RNA, single stranded DNA, double-stranded DNA followed by detection using an electrochemiluminescent labeled binding species.

10 Claims, 7 Drawing Sheets

Mix Sample and Reagents

Amplified Target Molecules

Hybridization and Antibody binding

Binding and Reading

Mix Sample and Reagents

Amplified Target Molecules using Biotinylated nucleotides

Hybridization

Binding and Reading

Mix Sample and Reagents

Amplified Target Molecules using Biotinylated Primers

Hybridization

Binding and Reading

Mix Sample and Reagents

Amplification Target Molecules

Hybridization

Binding and Reading

Mix Sample and Reagents

Amplified Target Molecules using ECL labeled nucleotides

Hybridization

Binding and Reading

Light generated

ECL labeled nucleotide for polymerase incorporation

6,048,687

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (xi) SEQUENCE DESCRIPTION: SEQ ID NO:1:

TTAAATTTTC CCATTAGCCC TATTGAGACT      30

(2) INFORMATION FOR SEQ ID NO:2:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (xi) SEQUENCE DESCRIPTION: SEQ ID NO:2:

AGAAATCTGT TGACTCAGAT TGGTTGCACT      30

(2) INFORMATION FOR SEQ ID NO:3:

```
    (i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:3:

TTAAATTTTC CCATTAGCCC TATTGAGACT                                          30

(2) INFORMATION FOR SEQ ID NO:4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:4:

TTAAATTTTC CCATTAGCCC TATTGAGACT                                          30

(2) INFORMATION FOR SEQ ID NO:5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:5:

AGAAATCTGT TGACTCAGAT TGGTTGCACT                                          30

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:6:

AGAAATCTGT TGACTCAGAT TGGTTGCACT                                          30

(2) INFORMATION FOR SEQ ID NO:7:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:7:

TAGAAGAAAT GATGACAGCA TGTCAGGGA                                           29

(2) INFORMATION FOR SEQ ID NO:8:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:8:

CAATGAGCCA AGTAACAAAT ACAGCTACC                                           29

(2) INFORMATION FOR SEQ ID NO:9:

(i) SEQUENCE CHARACTERISTICS:
```

```
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:9:

TAGAAGAAAT GATGACAGCA TGTCAGGGA                                    29

(2) INFORMATION FOR SEQ ID NO:10:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:10:

CAATGAGCCA AGTAACAAAT ACAGCTACC                                    29

(2) INFORMATION FOR SEQ ID NO:11:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:11:

TGTTAAAAGA GACCATCAAT GAGGA                                        25

(2) INFORMATION FOR SEQ ID NO:12:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:12:

GAATGGGATA GAGTGCATCC AGTGCATG                                     28

(2) INFORMATION FOR SEQ ID NO:13:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:13:

GACAGTGTAG ATAGATGACA GTCG                                         24

(2) INFORMATION FOR SEQ ID NO:14:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:14:

TGTTAAAAGA GACCATCAAT GAGGA                                        25

(2) INFORMATION FOR SEQ ID NO:15:

(i) SEQUENCE CHARACTERISTICS:
        (A) LENGTH: 24 base pairs
```

-continued (B) TYPE: nucleic acid
        (C) STRANDEDNESS: single
        (D) TOPOLOGY: linear (xi) SEQUENCE DESCRIPTION: SEQ ID NO:15:

TGTTAAAAGA GACCATCAAT GAGG                                                  24

(2) INFORMATION FOR SEQ ID NO:16:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:16:

GAATGGGATA GAGTGCATCC AGTGCATG                                              28

(2) INFORMATION FOR SEQ ID NO:17:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:17:

GAATGGGATA GAGTGCATCC AGTGCATG                                              28

(2) INFORMATION FOR SEQ ID NO:18:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:18:

GACAGTGTAG ATAGATGACA GTCG                                                  24

(2) INFORMATION FOR SEQ ID NO:19:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:19:

GACAGTGTAG ATAGATGACA GTCG                                                  24

CYCLING DNA/RNA AMPLIFICATION ELECTROCHEMILUMINESCENT PROBE ASSAY

This application is a continuation of, and claims priority from, U.S. patent application Ser. No. 08/124,686 filed Sep. 22, 1993 now abandoned.

FIELD OF THE INVENTION

This invention relates to an enhanced process for amplifying a specific nucleic acid sequence and its rapid detection and quantitation using electrochemiluminescent labeled binding species.

BACKGROUND OF THE INVENTION

Detection and quantitation of a specific nucleic acid sequence present in a sample is a known diagnostic method with great specificity. This specificity is based on the knowledge of the specific sequence and the generation of probes which are specific and complementary.

Methods for detection and quantitation of specific nucleic acid sequences are illustrated by the following patents: (1) U.S. Pat. No. 5,130,238 is directed toward an improved process for amplifying a specific nucleic acid sequence. The improvement of the amplification process involves the addition of dimethylsulfoxide (DMSO) alone or in combination with bovine serum albumin (BSA); (2) U.S. Pat. No. 4,683, 195 is directed toward a process for amplifying and detecting any target nucleic acid sequence contained in a nucleic acid or mixture thereof; (3) U.S. Pat. No. 4,683,202 is directed toward a process for amplifying any desired specific nucleic acid sequence contained in a nucleic acid or mixture thereof; (4) U.S. Pat. No. 4,486,539 is directed toward a method for identifying nucleic acids by a one-step sandwich hybridization test; and (5) WO 91/02814 is directed toward a process for amplifying a specific nucleic acid sequence.

The use of highly specific nucleic acid probes is in some cases the only method which can yield accurate results when the protein is absent, such as is the case for analysis of genetic defects such as cystic fibrosis. It is also valuable in the case of a latent viral infection such as HIV1 or herpes where little or no protein is produced by the infection. The great specificity of the nucleic acid probes also makes them valuable in the diagnosis of infectious agents which are difficult to identify with antibodies due to cross reaction and lack of cross reaction between isotypes of these agents. In addition, the analysis of DNA sequences allows the rapid and effective selection of a probe which will be specific. This is not possible with antibody-based reagents.

The greatest difficulty and limitation with applying existing nucleic acid probe technology is the complexity and slow methodology for the detection of specific sequences. With the amplification of nucleic acids, the limitations of nucleic acid probe methods associated with low levels of target molecules have been solved in U.S. Pat. Nos. 5,130, 238; 4,683,195; 4,683,202, identified above.

The use of natural amplification has been used in certain cases to remove this problem. This is exemplified by the use of ribosomal RNA with up to 100,000 copies per cell as taught in U.S. Pat. No. 4,851,330. This method, in order to be effective without the need to culture the infectious agent, makes use of a rapid chemiluminescence detection system which requires a number of incubations and washes. This method, however, is also limited only to selected cellular pathogens and is of no use in the case of viral or genetic defects.

Notwithstanding the amplification processes disclosed in the prior art, the present invention requires no pretreatment of the sample such as binding to solid phases or membranes, denaturing of the sample, purification of the sample by extraction of oil, protein or by gel electrophoresis and the probes can be added directly to the amplification mixture hybridized and analyzed. This was surprising in the light of the potential that the probe sequences would be modified or cause sample destruction mediated by the enzymes and conditions in the amplification mixture. For example, the presence of RNAase H, which degrades hybrids between DNA and RNA (the basis of the probe hybridization), degrades the specific hybrids in any attempt to probe the impure amplification mix. Also, the presence of reverse transcriptase would use the probes in the hybridization mixture as primers and remove them from the specific hybridization complex formation reaction. In addition to these potential problems, the buffer contains many compounds which might cause problems both for hybridization and also for the generation of ECL by the specific chemistries involved, for example, high levels of salts $MgCl_2$, KCl, nucleotides, dithiothreitol, spermidine, dimethyl sulphoxide, glycerol and proteins. This list contains many substances which interfere with other nucleic acid probe methods and would need to be removed to allow these methods to work, thus the present invention was surprisingly capable of carrying out a nucleic acid probe assay with such a simple protocol.

SUMMARY OF THE INVENTION

This invention relates to a diagnostics process for detection of specific nucleic acid sequences generated by amplification which is rapid, has fewer steps, and requires less user time than conventional diagnostic methods. The amplification takes place at a relatively constant temperature generating a plurality of single stranded RNA species. The hybridization to probes follows this amplification and is carried out at a relatively constant temperature followed by analysis for the bound or complexed electrochemiluminescent species. Hence, the diagnostic process is both rapid and sensitive unlike other systems which require multiple cycles of incubations and multiple washes followed by multiple incubations for detection of nucleic acid.

According to one aspect of the invention, a process for amplifying a specific nucleic acid sequence is used followed by the addition of two oligonucleotide probes—one with a binding species, the capture probe (i.e., biotin or antigen) and one with an electrochemiluminescent label.

The process involves the synthesis of single stranded RNA, single stranded DNA, and double stranded DNA. The single stranded antisense RNA is a first template for a second primer. The single stranded DNA is a second template for a first primer. The double stranded DNA is a third template for the synthesis of a plurality of copies of the first template. A sequence of the first or the second primer is sufficiently complementary to a sequence of the specific nucleic acid sequence and a sequence of the first or the second primer is sufficiently homologous to a sequence of the specific nucleic acid sequence. A second primer binds to the 3' end of the first RNA template and generates the second DNA template. A 3' end of the first primer hybridizes to the 3' end of the second DNA template. The second template is removed from the first template and is used to generate a complementary DNA strand. The resulting duplex DNA serves as a third template for synthesizing a plurality of first templates which in turn repeats the above described cycle. This process of amplification is described in detail by the following publications:

Kievits et al., 35 *J. Vir Method* 273–286 (1991); Bruisten et al., 9 *AIDS Res. and Human Retroviruses* 259–265 (1993); EP 0 329 822-A2, WO 91/02818, WO 91/02814 (an essentially similar method is also described in WO 88/10315). On completion of the incubation, as described above, samples from the said amplification are taken and a mixture of complementary probes and beads coated in a binding species complementary to one of the probes in hybridization buffer is added followed by incubation at a predetermined temperature to allow the hybridization of the probes to the said first template and the binding of one of the said probes to the beads via a binding interaction, i.e., antibody-antigen or biotin-streptavidin. On completion of the said incubation, a complex is formed which comprises the said first template generated from the amplification reaction as above hybridized to two said differing probe, one containing an electrochemiluminescent label and the other a binding species. This complex is further complexed to said coated bead which forms its complementary binding pair with the probe binding species. The resulting complex contains the amplified first template, the probe with its electrochemiluminescent label, the capture probe with its binding species, and the bead with its coating of binding species (see FIG. 1) all complexed via the specific interactions of each component. It will also be understood that the DNA sequences generated during the NASBA cycling will be targets for hybridization and detection.

In another embodiment of the claimed invention, the interaction between the probe and the bead can be made prior to the hybridization step by formation of a covalent bond to said bead or via a binding species (where said binding species is coated either by covalent or non-covalent methods) interaction or indirectly via a covalent bond to a species which can non-covalently coat said bead. An example of this indirect covalent coating could take the form of the probe being coupled to a carrier such as protein followed by coating via non-covalent methods to the bead surface.

In another embodiment, samples of the amplification would be mixed with a probe labeled with an ECL species and a bead which is coated with a binding species specific for the hybrid formed between said probe to the said amplified first template. For example, such a hybrid of DNA and RNA may be capture using a specific antibody. An example would be the use of an anti DNA:RNA antibody (U.S. Pat. No. 4,833,084, assigned to Miles, Inc.) Other antibodies which recognize such mixed hybrid molecules would also prove valuable such as those antibodies raised to hybrids of RNA or DNA to phosphonate, phosphorothioate, alkyl, or aryl phosphonate based nucleic acid sequences (Murakami et al., 24 *Biochemistry* 4041–4046 (1985), also available from Glenn Research, Sterling, Va.). These methods are based on the formation of a new molecular species on hybridization which is a binding species for an antibody and raising antibodies or other binding species to these molecular species.

In yet another embodiment, the assay method may also be used to quantitate the amount of nucleic acid in the starting material. This is achieved by the addition to the samples of specific 'spike' samples which are amplified during the reaction. The determination of the spike signal and sample signal allows a ratio to be calculated, which based on the original spike level, allows the determination of the sample level. This is most accurately determined by the use of multiple spikes which range in amount over the range of the potential sample amounts and allow the construction of a standard curve to give a reading at a ratio of 1:1 between target and sample. Methods based on this are well understood—Van Gemen et al., 43 *J. Vir. Methods* 177–187 (1993); Siebert and Larrick, 14 *Biotechniques* 244–249 (1993); Piatak et al., 14 *Biotechniques* 70–80 (1993). This method for quantitation is improved by the use of a rapid and accurate method for detection and quantitation provided by the use of the ECL labels and methods with the NASBA amplification.

The invention further provides a process for the detection of a specific nucleic acid sequence, comprising the steps of:

(a) Providing a single reaction medium containing reagents comprising
  (i) a first oligonucleotide primer,
  (ii) a second oligonucleotide primer comprising an antisense sequence of a promoter,
  (iii) a DNA-directed RNA polymerase that recognizes said promoter,
  (iv) an RNA-directed DNA polymerase,
  (v) a DNA-directed DNA polymerase,
  (vi) a ribonuclease that hydrolyses RNA of an RNA-DNA hybrid without hydrolyzing single or double-stranded RNA or DNA, (b) Providing in said reaction medium RNA comprising an RNA first-template which comprises said specific nucleic acid sequence or a sequence complementary to said specific nucleic acid sequence, under conditions such that a cycle ensues wherein
  (i) said first oligonucleotide primer hybridizes to said RNA first template,
  (ii) said RNA-directed DNA polymerase uses said RNA first template to synthesize a DNA second template by extension of said first oligonucleotide primer and thereby forms an RNA-DNA hybrid intermediate,
  (iii) said ribonuclease hydrolyses RNA which comprises said RNA-DNA hybrid intermediate,
  (iv) said second oligonucleotide primer hybridizes to said DNA second template,
  (v) said DNA-directed DNA polymerase uses said second oligonucleotide primer as template to synthesize said promoter by extension of said DNA second template; and
  (vi) said DNA-directed RNA polymerase recognizes said promoter and transcribes said DNA second template, thereby providing copies of said RNA first template; and thereafter (c) Maintaining said conditions for a time sufficient to achieve a desired amplification of said specific nucleic acid sequence, followed by the addition of;
  (i) at least one probe sequence complementary to said RNA first template labeled with an electrochemiluminescent species,
  (ii) at least one second capture probe sequence complementary to said RNA first template labeled with a binding species,
  (iii) a bead coated with a complementary binding species to said second probe sequence; and thereafter (d) Providing conditions of temperature and buffer to allow the hybridization of the probes to the said RNA first template and the binding of said binding species on said second capture probe with the complementary binding species on said bead to from a bead bound complex; and then (e) Detecting said bead bound complex using said electrochemiluminescent species.

The invention further provides a process for the detection of amplified products comprising the steps of:

(a) amplifying a sample nucleic acid under conditions to generate amplified product;

(b) mixing said amplified product with two binding species comprising (i) an ECL labeled binding species which interacts with a trimolecular complex with the amplified nucleic acid and bivalent binding species;

(ii) a bivalent binding species which interacts with a trimolecular complex with the amplified nucleic acid and ECL labeled binding species;

to form a binding complex reaction;

(c) incubating said binding complex reaction under conditions which allow the formation of a trimolecular complex of amplified product, ECL labeled binding species, and bivalent binding species;

(d) capturing said trimolecular complex via the bivalent binding species' remaining binding site to a solid phase; and (e) quantitating ECL label captured on the solid phase.

Definitions

In order to more clearly understand the invention, certain terms are defined as follows:

"Amplified product" means nucleic acid sequences generated by copying sample nucleic acid sequences multiple times using an enzymatic reaction.

"Annealing" refers to hybridization between complementary single chain nucleic acids when the temperature of a solution comprising the single chain nucleic acids is lowered below the melting or denaturing temperature.

"Binding species" means any species known to bind with another molecular species and are normally defined as a pair of species but may be formed from higher complexes, i.e., 3 or 4 which bind, i.e., antibody:antigen or oligonucleotide::antibody or oligonucleotide:antigen or DNA:DNA or DNA:RNA or RNA:RNA or DNA:RNA:DNA or Biotin-DNA:DNA-ECL labeled or receptor:ligand or DNA binding protein such as restriction enzymes, lac repressor.

The "complement" to a first nucleotide sequence is well known to be a second sequence comprising those bases which will pair by Watson-Crick hybridization with the first sequence. Thus, the complement to the deoxyribonucleic acid (DNA) sequence 5' ATGC 3' is well known to be 5'-GCAT 3'. For duplex, or double stranded DNA, each of the two strands are described as complementary to the other or as a complementary pair. The terms complement and anticomplement may also be used. With reference to the identification of the strand of duplex DNA from which transcription to RNA proceeds, the transcription strand is generally described as plus and its complement as minus ("+" and "−"), or the transcription strand may be described as the sense strand, and its complement as antisense. Two strands each hybridized to the other having all base pairs complementary, are 100% complementary to each other. Two strands, each hybridized to the other, having 5% of bases non-complementary, are 95% complementary (or the two strands have 95% complementarity). In addition, it will also be understood that nucleic acid sequences can form triple helix structures based on a specific interaction of three strands which would be considered to complementary in a specific way to each other within this triple stranded hybrid.

The terms "detection" and quantitation" are referred to as "measurement", it being understood that quantitation may require preparation of reference compositions and calibrations.

"Electrochemiluminescent (ECL) species" means any compound known to electrochemiluminescense;

"Electrochemiluminescent (ECL) labels" are those which become luminescent species when acted on electrochemically. Electrochemiluminescent techniques are an improvement on chemiluminescent techniques. They provide a sensitive and precise measurement of the presence and concentration of an analyte of interest. In such techniques, the sample is exposed to a voltammetric working electrode in order to trigger luminescence. The light produced by the label is measured and indicates the presence or quantity of the analyte. Such ECL techniques are described in PCT published application by Bard et al. PCT Appl. No. US 85/02153, entitled "Luminescent Metal Chelate Labels and Means for Detection" and Massey et al. PCT Appl. No. US 87/00987, entitled "Electrochemiluminescent Assays"; PCT Appl. No. US 88/03947, Publication No. WO 89/04302 "Electrochemiluminescent Moieties and Methods for Their Use"; Hall et al., "Method and Apparatus for Conducting Electrochemiluminescent Measurements", U.S. Appl. Ser. No. 744,890 filed Aug. 14, 1991; and Zoski and Woodward. "Apparatus for Conducting Measurements of Electrochemiluminescent Phenomena", PCT US 89.04854 corresponding to pending EPO Appl. No. 89/912913.4, Publication No. 0441880.

Examples of ECL tags are tag NHS (N-hydroxysuccinimide) and tag phosphoramidite. The tag-NHS ester is useful for labeling substances containing free amino groups capable of reaction with the NHS ester to form an amide bond. (See, for example, WO 86/02734.) The tag phosphoramidite (Gudibande et al. U.S. Appl. Ser. No. 07/805,537 entitled "Improved Electrochemiluminescent Label for DNA Probe Assay" which is hereby incorporated herein by reference) is useful for labeling substances containing free amino, sulphydryl, or hydroxyl groups forming phosphor-linkages especially phosphodiester linkages.

An "ECL assay buffer" is a general diluent which contains tripropylamine that is necessary for the electrochemical reaction on the electrode in an ECL analyzer.

An "ECL diluent" is a diluent reagent used in diluting solutions containing labile biomolecules for storage purposes.

"ECL apparatus" is any apparatus for performing electrochemiluminescence based assays. Such ECL apparatus are described in PCT Appl. No. US 85/02153 by Bard et al. entitled "Luminescent Metal Chelate Labels and Means for Detection" and in PCT Appl. No. US 87/00987 by Massey et al. entitled "Electrochemiluminescent Assays"; PCT Appl. No. US 88/03947, Publication No. WO 89/04302 "Electrochemiluminescent Moieties and Methods for Their Use"; Hall et al. "Method and Apparatus for Conducting Electrochemiluminescent Measurements", U.S. Appl. Ser. No. 744,890; and Zoski, G., and S. Woodward. "Apparatus for Conducting Measurements of Electrochemiluminescent Phenomena", PCT US 89.04854 corresponding to pending EPO Appl. No. 89/912913.4, Publication No. 0441880.

"Homology" between polynucleotide sequences refers to the degree of sequence similarity between the respective sequences. Two strands which are identical in sequence have 100% sequence homology. Two strands which differ by 5% of sequences have 95% sequence homology. The greater the degree of homology between two strands A and B, the greater the complementarity between A and the complement of B.

"Hybridization" describes the formation of double stranded or duplex nucleic acid from complementary single stranded nucleic acids. Hybridization may take place between sufficiently complementary single stranded DNA and/or RNA to form: DNA:DNA, DNA:RNA, or RNA:RNA or DNA:RNA:DNA or Biotin-DNA:RNA:DNA-ECL label. This may also include sequences of nucleotides which are linked using modified natural chemistries such as phosphonate, phosphorothioate, alkyl or aryl phosphonate based nucleic acid sequences (Murakami et al., *Biochemistry* 24 (1985):4041–4046, also Glenn Research, Sterling, Va.).

The term "label" or "labeled" when applied to a nucleic acid means that the nucleic acid in question is linked to a moiety which is detectable by its properties which may include: ECL and luminescence, catalysis of an identifying chemical substrate, radioactivity, or specific binding properties. Thus, the term "label" includes ligand moieties unless specifically stated otherwise.

It is also well know to the art that the term "nucleic acid" refers to a polynucleotide of any length, including DNA or RNA chromosomes or fragments thereof with or without modified bases as described herein.

A "nucleotide" is at least one of the following bases: adenine, cytosine, guanine, thymine or uracil, plus a sugar (deoxyribose for DNA, ribose for RNA), plus a phosphate. In order to provide monomers for the DNA polymerization reaction, typically all four of the deoxynucleotide triphosphates are required. A nucleotide, as defined herein, may also include modified bases such as 5-methyl-dCTP and 7-deaza-dGTP used to improve the action of polymerase on templates. The term nucleotide as used herein also includes bases linked to biotin and digoxigenin (Digoxigenin-11-UTP from Boehringer Mannheim, Indianapolis, Ind.) and biotin-21-UTP and amino-7-dUTP (Clontech, Palo Alto, Calif.) and ECL labeled nucleotide (see FIGS. 6 and 7) which may be incorporated directly into a primer or into a primer extension product during amplification, to provide for selective binding of amplified sequences.

An "oligonucleotide" is a sequence formed of at least two nucleotides.

A "polynucleotide" is a long oligonucleotide and may be either RNA and DNA.

While the term oligonucleotide is generally used in the art to denote smaller nucleic acid chains, and "polynucleotide" is generally used in the art to denote larger nucleic acid chains including DNA or RNA chromosomes or fragments thereof, the use of one or the other term herein is not a limitation or description of size unless expressly stated to be.

A "primer" is a relatively short segment of oligonucleotide which is complementary to a portion of the sequence of interest (the sequence of interest can be a subfragment within a larger nucleic acid sequence). A primer represents a 5' terminus of the resulting extension product. A primer which is complementary at its 3' terminus to the sequence of interest on the template strand enables this 3'terminus to be acted on by a polymerase on hybridization to the template. It is well known that modifications to the 3' end will affect the ability of an oligonucleotide to function as primer. An example is the incorporation of a dideoxynucleotide as in DNA sequencing thus preventing the action of DNA polymerases. It is well known that the length of the primer will depend upon the particular application, but that 20–30 base pairs is a common size. As is well known, a primer need not be a perfect complement for successful hybridization to take place. If the primer is an imperfect complement, an extension product will result which incorporates the primer sequence, and during a later cycle, the complement to the primer sequence will be incorporated into the template sequence. Thus, it is well known that a properly selected primer having a sequence altered from that of the complement of the template may be used to provide in vitro mutagenesis. The primer may incorporate any art known nucleic acid bases, including any art known modified or labeled bases as defined above so that the primer extension product will incorporate these features to permit separation and detection of the primer extension product. A tag or marker advantageously linked to a primer may include an ECL fluorescent or luminescent tag, an isotopic (e.g., radioisotope or magnetic resonance) label, a dye marker, an enzyme marker, an antigenic determinant detectable by an antibody, or a binding moiety such as biotin enabling yet another indicator moiety such as a streptavidin coated bead to specifically attach to the primer or any nucleic acid sequence incorporating that primer. When the labeled or tagged amplification product is formed, that amplification product may be detected by the characteristic properties of the tag or label.

The term "primer extension product" describes the primer sequence together with the complement to the template produced during extension of the primer.

A "probe" is a single or double stranded nucleic acid which has a sequence complementary to a target nucleic acid sequence of interest and which has some additional feature enabling the detection of the probe—target duplex. One skilled in the art will understand that if the probe and/or the target is double stranded, the double stranded nucleic acid must undergo strand separation before hybridization can take place. It is possible, if a triple strand formation is used, then the double stranded target will not need to be rendered single stranded prior to hybridization.

A probe is rendered detectable by an attached tag or marker. A tag or marker linked to a probe may include a fluorescent, ECL or luminescent tag, an isotopic (e.g., radioisotope or magnetic resonance) label, a dye marker, an enzyme marker, an antigenic determinant detectable by an antibody, or a binding moiety such as biotin enabling yet another indicator moiety such as a streptavidin coated bead to specifically attach to the probe. When the labeled or tagged probe—target duplex is formed, that duplex may be detected by the characteristic properties of the tag or label. Alternatively, as described for the ECL assays in the following examples, the probe with its binding moiety allows the capture of labeled target, via hybridization and duplex formation, allowing detection by a label or other art known means.

"Sample" means a mixture containing nucleic acids.

A "sequence" (e.g., sequence, genetic sequence, polynucleotide sequence, nucleic acid sequence) refers to the actual enumerated bases (e.g., ribose or deoxyribose) present in a polynucleotide strand (e.g., reading from the 5' and 3' direction) and the relative position of these bases with respect to each other.

The term "single primer" means a single, unpaired, specific or selected primer designed to selectively hybridize with a target nucleic acid sequence of interest.

"Specific nucleic acid sequence" means a single stranded or double stranded nucleic acid which one could use as a probe or amplify.

A "specific or selected" nucleotide sequence refers to a particular sequence distinguishable (i.e., by hybridization analysis) from other difference sequences (e.g., the specific nucleotide sequence 5'-ATGCCC-3' is not the same sequence as 5'-AAGCCC-3').

A specific or selected primer is one which is designed to hybridize with a particular template sequence to achieve the desired result by making the primer complementary or approximately complementary to the 3' terminal of the template sequence. The specific primer will selectively achieve the desired result even if the target template sequence is present in a mixture of many other nucleic acid sequences.

The specific or selected primer is distinguished from a "universal primer" which will indiscriminately anneal to any DNA sequence to which a complementary (to the primer) adaptor terminal sequence has been attached. With a universal primer, care must be taken to isolate the nucleic acid of interest, or otherwise direct the ligation procedure only to the desired DNA sequence of interest, to avoid randomly attaching the adaptor to all nucleic acid sequences present.

A "strand" is a single nucleic acid sequence. Thus, a duplex or double stranded chromosome, chromosome fragment or other nucleic acid sequence may be separated into complementary single strands.

"Strand separation" refers to the conversion of a double stranded or duplex nucleic acid to two complementary single stranded polynucleotide. The separation process may employ well known techniques including: enzyme mediated separation (e.g., by the enzyme helicase, physical-chemical separation (pH, ionic concentration and the like), and thermal separation also known as thermal denaturing. Thermal denaturing (also referred to as "melting") is the separation of a double stranded polynucleotide (fully or partially duplex) into at least two single strands of polynucleotide by raising the temperature of the solution holding that polynucleotide.

"Sufficiently complementary" means that two nucleic acids are capable of specific interaction which allows either a primer dependent and template directed synthesis of DNA or a probe to bind to nucleic acid sequence.

A "template" is any sequences of nucleic acid upon which a complementary copy is synthesized. This may, in general, be DNA to DNA replication, DNA to RNA transcription, or RNA to DNA reverse transcription. A DNA template provides the sequence information for extension of the complementary primer by the DNA polymerase reaction. An RNA template may provide the sequence information for extension of a complementary DNA primer by an analogous reaction catalyzed by the enzyme reverse transcriptase As is well known to the art, the template may be found in a single or double stranded form. If the template enters the amplification process in the double stranded form, the template strand will not hybridize to its complementary primer until it is denatured by the first thermal denaturing cycle. If the template enters the amplification process already in the single stranded form, the primer will hybridize (described as annealing when thermal cycling is utilized) with its complementary template before the first thermal denaturing step.

DETAILED DESCRIPTION OF THE PREFERRED EMBODIMENTS

This invention relates to a process for amplifying a specific nucleic acid sequence and its rapid detection and quantitation. The amplification involves an alternate synthesis for DNA and RNA. In this process, single stranded antisense (−) RNA is converted to single stranded DNA which in turn is converted to dsDNA and becomes a functional template for the synthesis of a plurality of copies of the original single stranded RNA. A first and a second primer are used in the amplification process. A sequence of the first primer or the second primer is sufficiently complementary to a sequence of the specific nucleic acid sequence and a sequence of the first or the second primer is sufficiently homologous to a sequence of the specific nucleic acid sequence. If the specific nucleic acid sequence is double stranded, then the primers can both be complementary and homologous. The detection, of the specific sequences which are amplified, is achieved by the use of probe sequences which form hybrids with the amplification products either DNA or RNA. These probe sequences are generally sufficiently complementary to a sequence of the specific nucleic acid sequence which results in the formation of a specific hybrid. These hybrids are then detected by the use of an ECL detection instrument which allows the ECL label to generate light in a controlled fashion at the surface of an electrode allowing both its detection and quantitation (FIGS. 1, 2, 3, 4, 5, 6).

Figure 1:
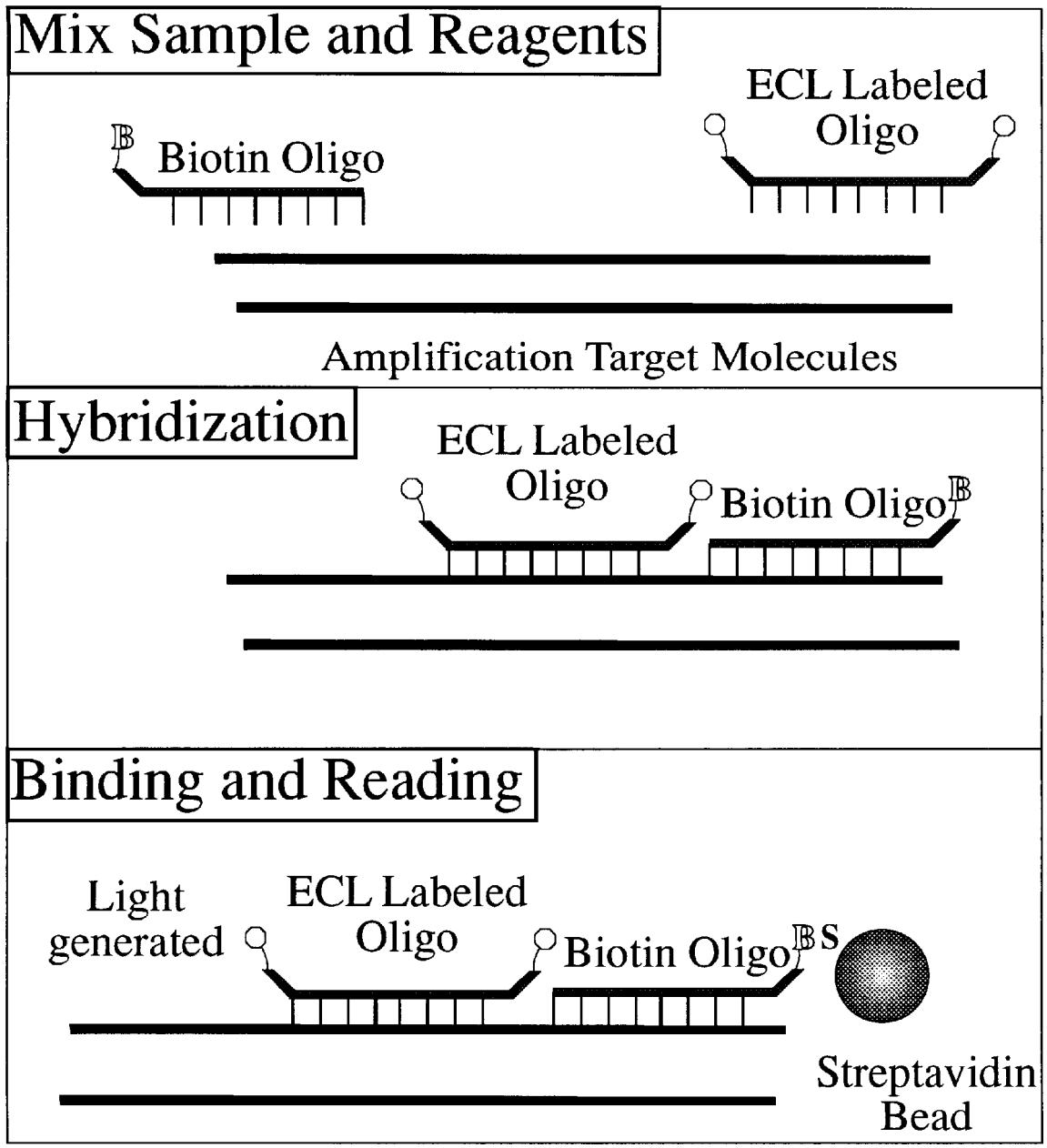
FIG. 1 is a general illustration of the nucleic acid hybridization process of the invention. Biotin labeled oligonucleotide probe along with ECL labelled oligonucleotide probe are mixed with a sample containing amplified target molecule conditions to form the complex shown. The illustrated probes bind specifically to distinct portions of the amplified target molecule. The strepavidin coated bead is separately reacted with the complex previously formed to form a second complex. The second complex is separated and/or contacted with an electrode surface (not shown) to induce light formation.

The assays for these amplified products is possible using a number of formats. The preferred method makes use of two probe molecules after the amplification process one is labeled with a binding species (i.e., biotin, digoxin, fluorescein), the other probe is labeled with an ECL label (i.e., Ru chelate, Os chelate, Re, Rh). These probes are added to the sample from the amplification reaction which generates a plurality of RNA copies of the original single stranded RNA or DNA and are complementary or sufficiently complementary to the plurality of RNA copies of the original single stranded RNA or DNA. This mixture of probes and amplified nucleic acid are allowed to hybridize by the control of the temperature and buffer components which are selected for the specific probe and plurality of RNA copies of the original single stranded RNA or DNA using methods known to those skilled in the art. The formation of these hybrids allows both probes to be linked in the same hybrid complex. These are then captured from the incubation by the addition of the magnetic beads which are coated with a binding species which binds to the binding species on the capture probe (FIG. 1). For example, with biotin on the probe streptavidin or avidin might be coated on to the magnetic beads or with digoxigenin on the probe an antibody specific for digoxigenin would be coated on the bead. This mixture of the hybrid complex and the bead would then be incubated under conditions known to promote the binding interaction of the binding species. These conditions for binding of binding species are well known to those skilled in the art; for example, biotin to streptavidin or avidin and antigen antibody interactions.

Following the capture of the hybrid complex on the magnetic beads, the sample may be washed by capture of the beads by a magnet used in close proximity to the sample tube, or more ideally, the sample would be sampled directly into an ECL instrument which would capture the magnetic beads and its bound complex followed by the electrochemical reaction of the surface bound ECL label. The light generated from this electrochemical reaction is measured and used to determine the amount of ECL label which has formed a complex with the bead. This determination of the relative amounts of ECL label bound to the beads under certain conditions allows a determination of the amount of the plurality of RNA copies of the original single stranded RNA or DNA generated in the amplification. Using this information regarding the level of amplification of the specific DNA or RNA allows the diagnosis of the sample DNA or RNA for the presence of a specific DNA or RNA sequences which determine the presence of a gene and or organism in a sample.

Alternative to the above method, we may make use of two oligonucleotides which are labeled with binding species which allow the formation of a hybrid complex as described above but without a ECL label attached directly to the probe oligonucleotide. In this alternative format, the ECL label is linked to the hybrid complex either before hybridization to for said complex or after by the formation of a binding pair complex. Examples of such a system would be the use of a probe labeled with digoxin (binding species or antigen) and a probe labeled with biotin (binding species) these two probes would under well known conditions from a hybrid complex with the plurality of RNA copies of the original single stranded RNA or DNA generated in the amplification. After the formation of this hybrid complex, the addition of ECL labeled anti-digoxin antibody (complementary binding species or specific antibody) and streptavidin (complementary binding species) coated magnetic beads under conditions known to allow the formation of binding interactions (pH 4–9, 1 mM to 2M salts, 0 to 10% detergents) allows the linkage of the ECL label to the hybrid complex by the binding of antigen to antibody. Also the complex is captured onto the surface of the bead via the binding interaction of streptavidin to biotin. The resulting extended complex of probes hybridized to the plurality of RNA copies of the original single stranded RNA or DNA generated in the amplification is then analyzed by the use of an ECL analyzer.

Figure 2:
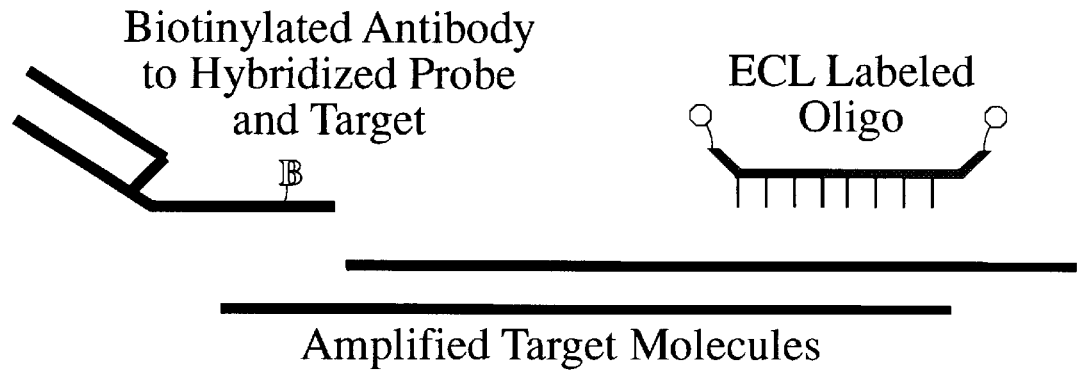
FIG. 2. is a general illustration of an alternative nucleic acid hybridization process wherein a biotinylated antibody is used as a detectant for the oligonucleotide ECL labeled probe—amplified target molecule complex (I). The antibody, prepared using conventional techniques, specifically binds with the oligonucleotide—amplified target molecule complex.
Figure 2:
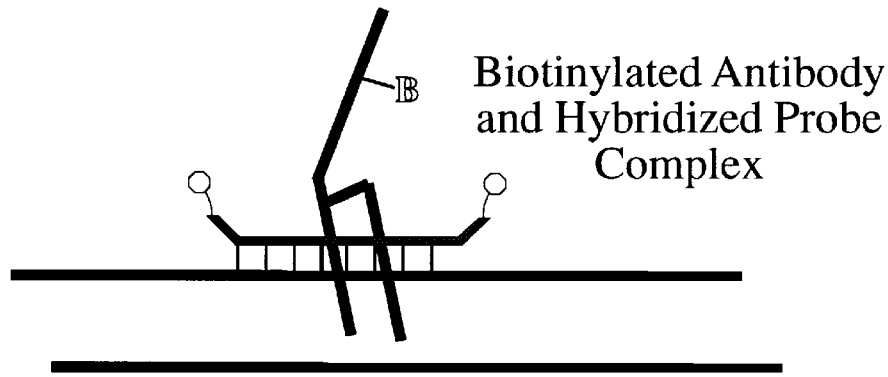
Figure 2:
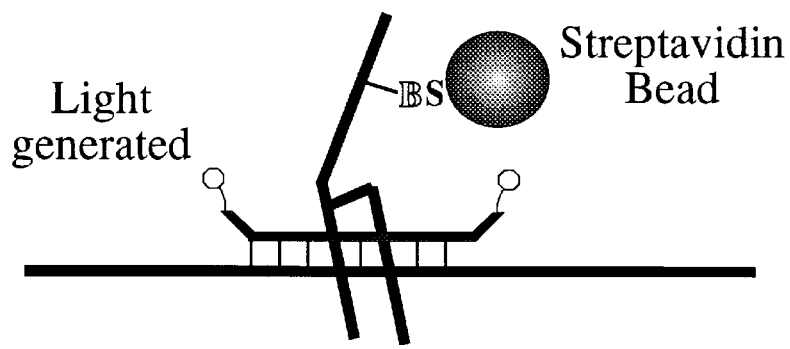
Figure 3:
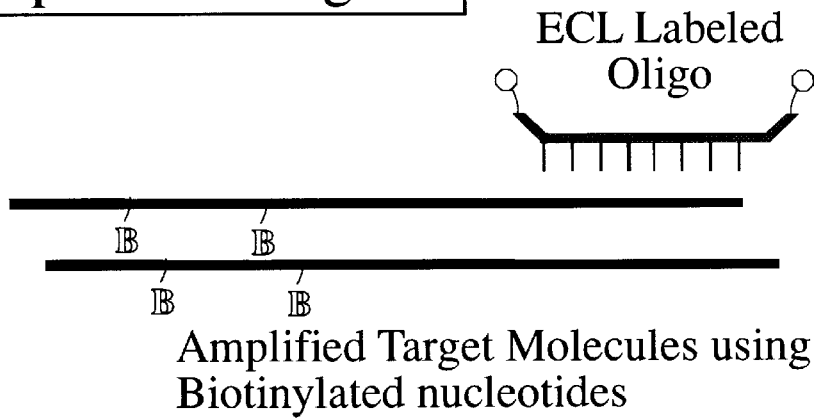
FIG. 3 is a general illustration of an alternative nucleic acid hybridization process wherein a biotinylated nucleotide is incorporated into the amplified target molecule during the NAMBA™ or NAMBA™-like amplification stage (see, for example, Kievitz et al. reference cited previously) which results in the formation of the amplification mixture from which the sample aliquot is taken. The biotinylated amplified target molecule as shown forms a complex with strepavidin coated beads.
Figure 3:
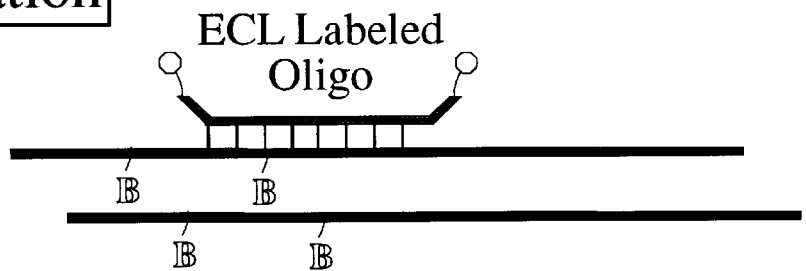
Figure 3:
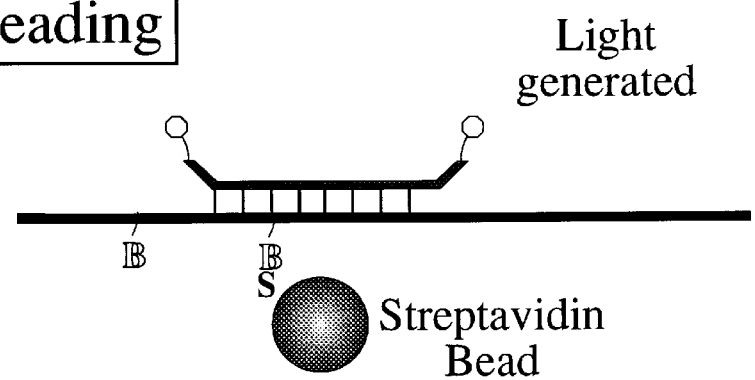

Alternatively, the formation of a specific complex labeled with an ECL species could be achieved by the use of a probe sequence labeled with an ECL species which when hybridized to the plurality of RNA copies of the original single stranded RNA or DNA generated in the amplification forms a binding species. This hybrid complex, or said binding species, is then captured by using complementary binding species coated magnetic beads followed by analysis using an ECL analyzer. For example, antibodies to DNA:RNA hybrids (FIG. 2).

Figure 4:
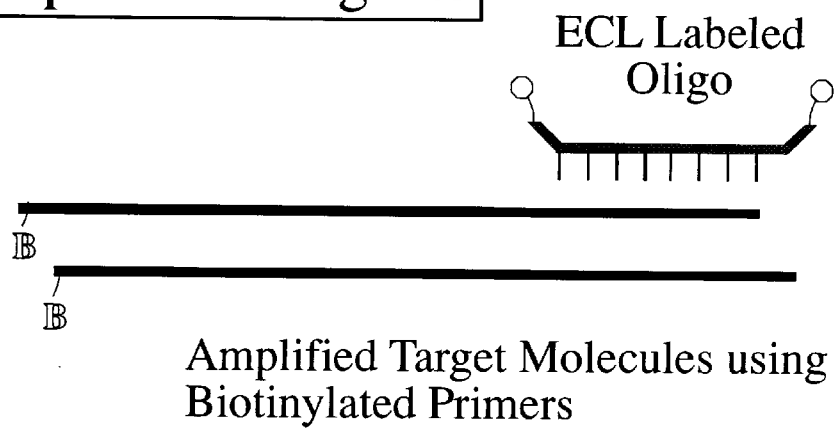
FIG. 4 is a general illustration of an alternative nucleic acid hybridization process the binding species is incorporated into the amplified target molecule via a biotinylated primer used in one of the NAMBA™ or NAMBA™-like amplification stage.
Figure 4:
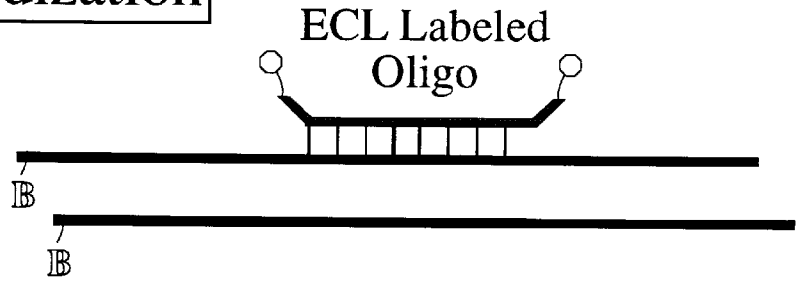
Figure 4:
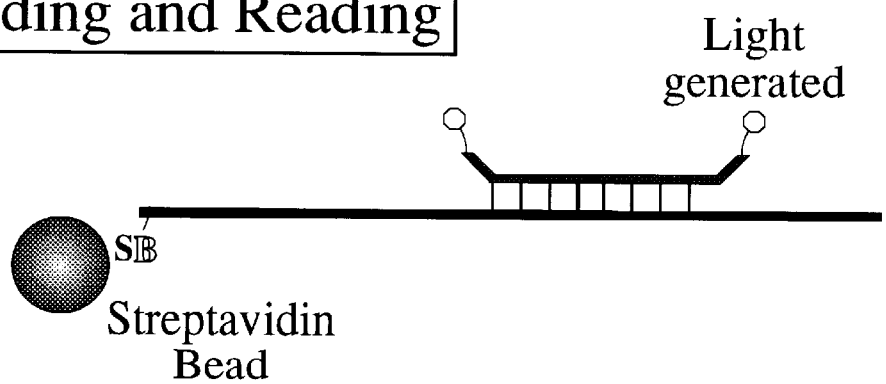
Figure 7:
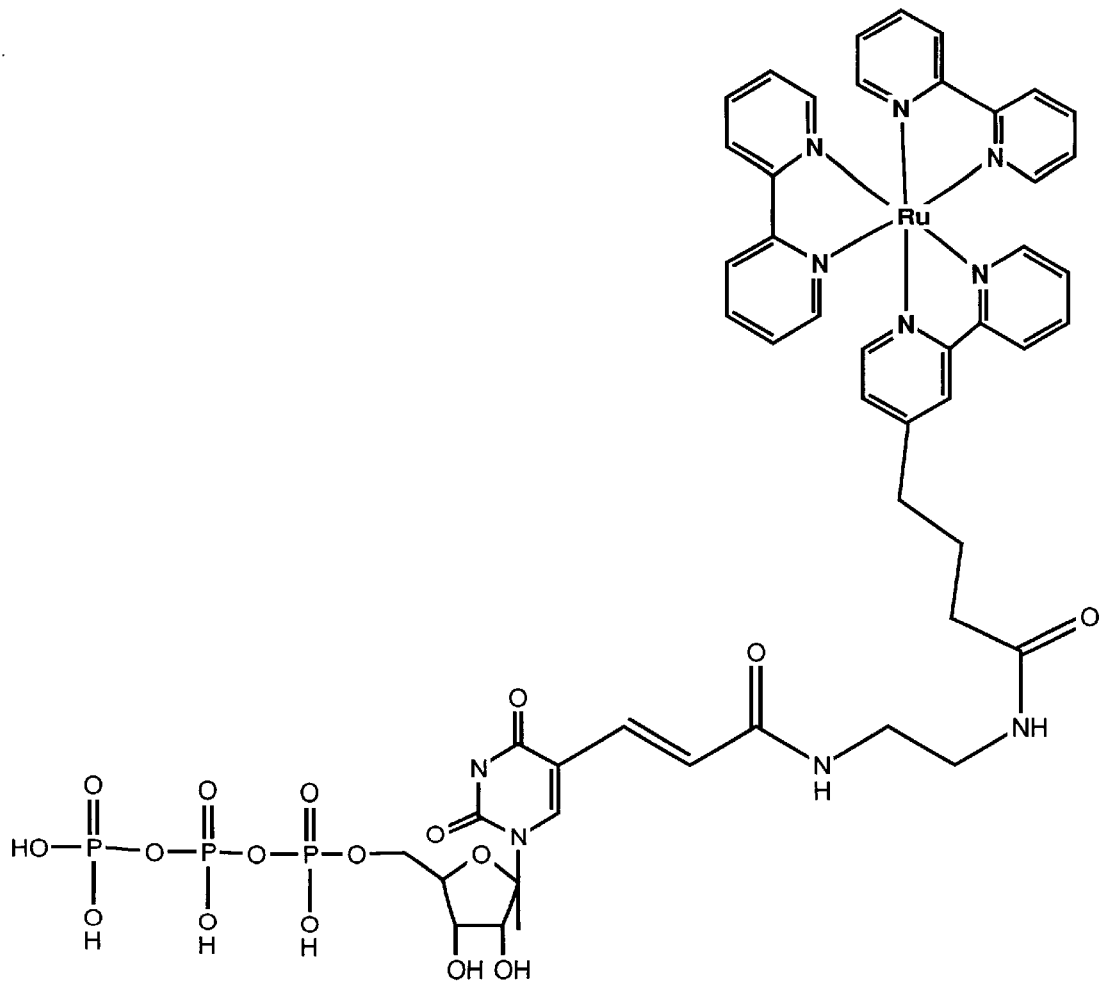
FIG. 7 is an ECL labeled nucleotide.

Alternatively, the amplification could be performed with a binding species such that said binding species are incorporated into the plurality of DNA and/or RNA molecules generated during the amplification process. Methods for this are well known to those skilled in the art. Examples of this could be the use of a primer (see primer 2, U.S. Pat. No. 5,130,238) modified to include a binding species said primer is then incorporated into the DNA+ strand by the action of RT on the RNA− species and primer 2. The DNA+ product would be a DNA+ species covalently linked to a binding species molecule. This DNA-binding species molecule could then be hybridized to an ECL labeled probe and captured onto beads via a complementary binding species for ECL analysis (FIG. 4). In the same format, the DNA-binding species molecule could be captured onto a bead by hybridization, followed by binding to the DNA-binding species with a complementary binding species labeled with an ECL label. An example of the binding species could be biotin and its complementary binding species streptavidin. It will be understood that the RNA− and DNA+ (FIG. 1) could be labeled with a binding species by inclusion of a nucleotide as described earlier which is modified to incorporate a binding species for example biotin and digoxigenin (Digoxigenin-11-UTP from Boehringer Mannheim, Indianapolis, Ind.), and biotin-21-UTP and amino-7-dUTP (Clontech, Palo Alto, Calif.) and ECL labeled nucleotides (FIG. 7) into the amplification reaction. The resulting DNA+ and/or RNA-binding species molecules can then be used in the assay formats as described above (FIG. 3).

Figure 5:
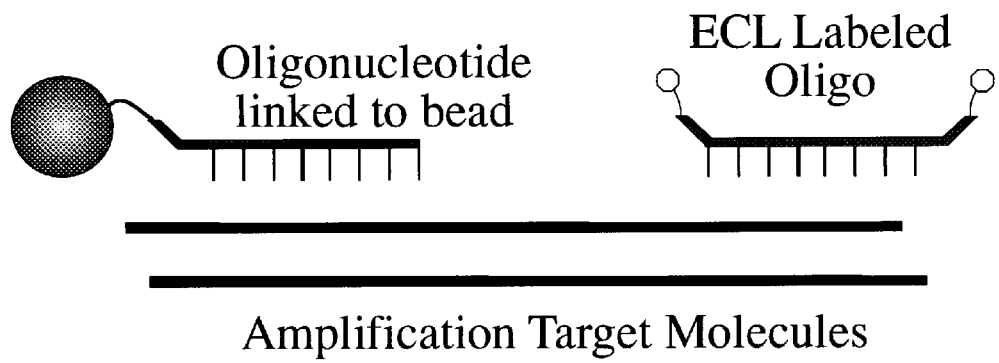
FIG. 5 is a general illustration of an alternative nucleic acid hybridization process the oligonucleotide probe is linked to the bead directly or indirectly through a covalent bond or a specific binding pair moiety.
Figure 5:
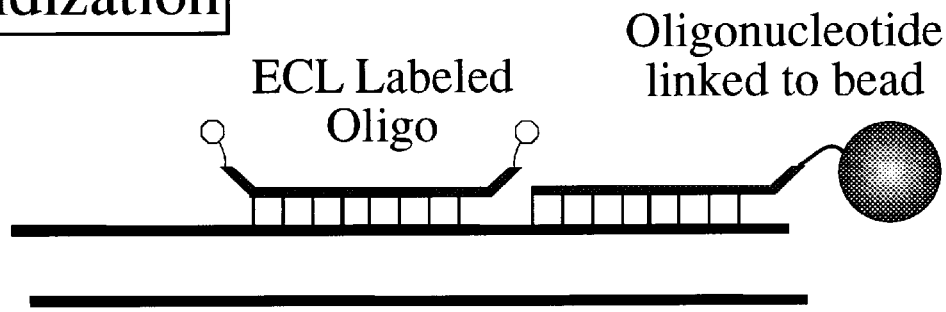
Figure 5:
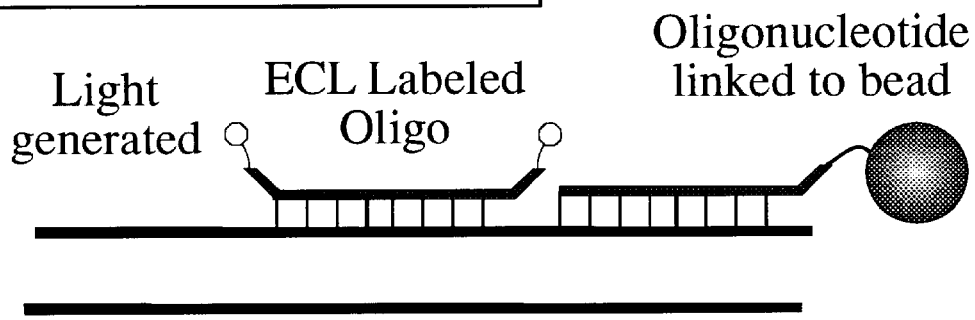
Figure 6:
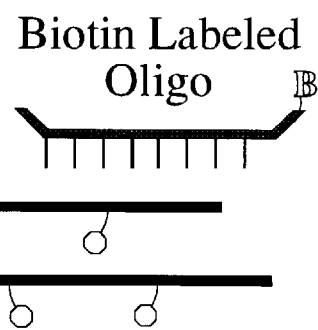
FIG. 6 is a general illustration of an alternative nucleic acid hybridization process wherein the ECL label(s) is (are) incorporated into the amplified target molecule during a previous amplification cycle in an NAMBA™ or NAMBA™-like process.
Figure 6:
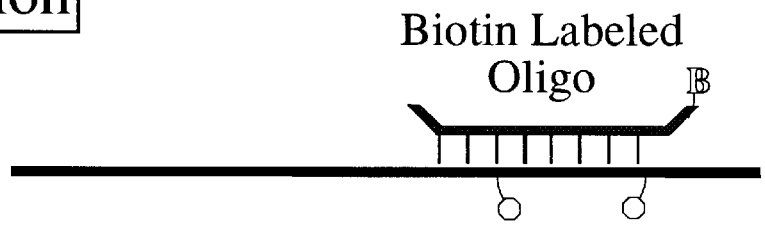
Figure 6:
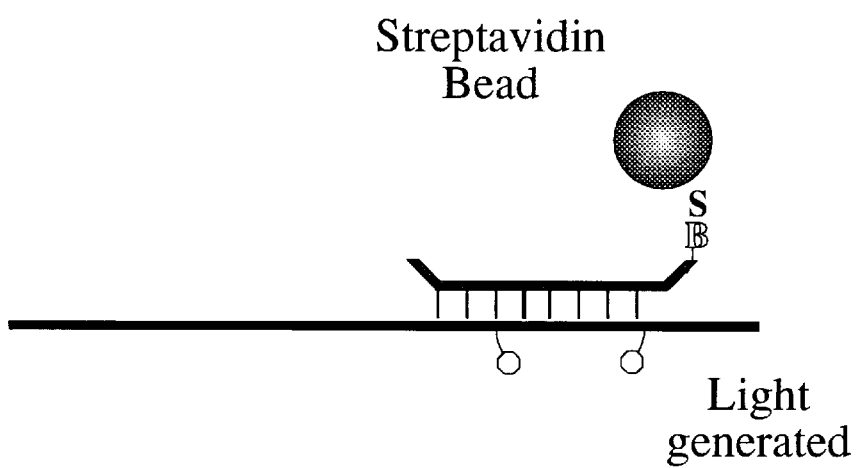

Beads which are used in this assay are typically those from Dynal M450 and M280 coated with streptavidin but other beads can be used so long as the beads can be para-magnetic and are in the size range from 0.5 $\mu$m to 10 $\mu$m. It will be understood to one of ordinary skill in the art that the capture oligonucleotide could be coupled to these beads obviating the need for a binding species (FIG. 5).

Having now generally described the invention, the following examples are included for purposes of illustration and are not intended to limit the scope of the invention.

EXAMPLES

Example 1:
Oligonucleotide Synthesis and Labeling

The oligonucleotides were made on an Applied Biosystems (San Jose, Calif.) automated oligonucleotide synthesizer using the β-cyanoethyl phosphoramidite chemistry (Beaucage and Caruthers 22 *Tetrahedron Lett.* 1859–62 (1982)). Oligonucleotide amino modifications to the 5' end occurred at the last coupling step. Clontech (San Diego, Calif.) supplied the amino modifiers, See U.S. Pat. 5,141, 813. The resulting 5' modified oligonucleotides all contain a six carbon spacer arm to the amino group, designated (C6, NH2).

All the synthetic oligonucleotides were purified to remove any contaminating amino groups by gel filtration on a BIOGEL™ P6 (Bio-Rad Labs, Richmond, Calif.) column. Biotin was introduced via the 5'-amino group of the oligonucleotides using NHS-biotin (Clontech, San Diego, Calif.). Tag-NHS ester label (an NHS ester of the Ru tris bipyridyl complex) was introduced via the amino group of the modified oligonucleotides as follows. The oligonucleotides (0.1 $\mu$mole) in 100 $\mu$l of PBS (pH 7.4) were reacted with 0.5

μmole of tag-NHS ester label dissolved in DMSO overnight at room temperature in the dark. Oligonucleotides were recovered from these labeling reactions by ethanol precipitation. The modifications to the oligonucleotide and the labeling are indicated as follows. Biotin:linker:'oligonucleotide' to indicate an oligonucleotide modified with a 5' amino group and then reacted with a biotin NHS reagent to yield a 5' biotinylated oligonucleotide. Also R:linker:'oligonucleotide' to indicate an oligonucleotide modified with a 5' amino group and then reacted with the ruthenium tris bypyidine NHS reagent to yield a 5' ruthenium chelate oligonucleotide. Also 'oligonucleotide':linker:R to indicate an oligonucleotide modified with a 3' amino group and then reacted with the ruthenium tris bypyidine NHS reagent to yield a 3' ruthenium chelate oligonucleotide.

Probes for the Pol2 assay were as follows:
OT1, TTAAATTTTCCCATTAGCCCTATTGAGACT (SEQ ID NO:1) HIV1 Genbank; HIV BH102 #1900–1929 and
OT2, AGAAATCTGTTGACTCAGATTGGTTGCACT (SEQ ID NO:2) HIV1 Genbank; HIV BH101 #1869–1898.

These were made with the following modifications:
5OT1, Biotin:linker:TTAAATTTTCCCATTAGCCCTATTGAG ACT(SEQ ID NO:3)
3 5OT1, R:linker:TTAAATTTTCCCATTAGC-CCTATTGAGACT :(SEQ ID NO:4) linker: R
5OT2, Biotin:linker:AGAAATCTGTTGACT-CAGATTGGTTG CACT(SEQ ID NO:5)
3 5OT2, R:linker:AGAAATCTGTTGACTCAGAT-TGGTTGCAC T:(SEQ ID NO:6)linker: R.

Amplification was as described in *J. Vir. Methods* 35 (1991) :273.

Probes for the GAG3 assay were as follows:
Sequences for analysis of the HIV1 gag gene, Genbank HIVBH102 #1139–1167
AKZO1 TA GAA GAA ATG ATG ACA GCA TGT CAG GGA (SEQ ID NO:7) (29 bases)
HIVBH102 #1208–1236
AKZO2 CA ATG AGC CAA GTA ACA AAT ACA GCT ACC (SEQ ID NO:8)
made as:
AKZO1, Biotin:linker TA GAA GAA ATG ATG ACA GCA TGT CAG GGA (SEQ ID NO:9)(29 bases) and
AKZO2 R:linker:CA ATG AGC CAA GTA ACA AAT ACA GCT ACC (SEQ ID NO:10):linker R (29 bases) for the gag3 assays below. The amplifications were performed or described in Van Gemen et al. 43 *J. Vir. Methods* 177–187 (1993).

Further probes for quantitative gag assays were as follows:
Probe A: TGT TAA AAG AGA CCA TCA ATG AGG A (SEQ ID NO:11) (25 bases) genbank ref. HIVBH102 #710–734.
Probe B: GAA TGG GAT AGA GTG CAT CCA GTG CAT G (SEQ ID NO:12) (29 bases) genbank ref. HIVBH102 #742–769.
Probe C: GAC AGT GTA GAT AGA TGA CAG TCG (SEQ ID NO:13) (24 bases) control sequence for quantitation as described in Van Gemen et al. *J. Vir. Methods* (1993).

The use of these probes A, B, and C would be as follows:
Using A as capture and B, C as detection or B, C as capture and A as detection.
To generate the needed probes, the following sequences were made incorporating biotin (binding species) and the ruthenium tri bypyridine complex (ECL label).

Probe A made as:
AKZO-A2, R:linker:TGT TAA AAG AGA CCA TCA ATG AGG A(SEQ ID NO:14):linker:R
and as AKZO-A1, Biotin:linker:TGT TAA AAG AGA CCA TCA ATG AGG(SEQ ID NO: 15).
Probe B made as:
AKZO-B2, R:linker:GAA TGG GAT AGA GTG CAT CCA GTG CAT G(SEQ ID NO: 16):linker:R
and as AKZO-B1, Biotin:linker:GAA TGG GAT AGA GTG CAT CCA GTG CAT G(SEQ ID NO:17).
Probe C made as:
AKZO-C2, R:linker:GAC AGT GTA GAT AGA TGA CAG TCG(SEQ ID NO:18):linker:R
and as AKZO-C1, Biotin:linker:GAC AGT GTA GAT AGA TGA CAG TCG(SEQ ID NO: 19).
Where R is the ruthenium trisbypyridine N-hydroxy succinamide ester reacted to an amino group on the oligonucleotide. The amino group introduced during synthesis.

Example 2:
Preparation of Streptavidin Magnetic Beads

To 15 mg of BSA (in 2–3 ml PBS), 105 μl of dimethylsulfoxide containing 50 mg/ml of biotin-x-NHS (Clontech, San Diego, Calif.) was added followed by mixing and incubation at room temperature for 30 minutes. The reaction was stopped by adding 30 μl of 1M glycine and incubation at room temperature for 10 minutes. The reaction mix was purified by gel filtration chromatography (Bio-Gel P6, Biorad Labs, Richmond, Calif.). This biotin-BSA was filtered using a 0.2 μm filter and syringe. 5 mg biotin-BSA in 10 ml of 0.2 M sodium carbonate/bicarbonate buffer pH 9.6 was added to 300 mg of DYNABEADS™ (DYNAL No. 14002) (DYNABEADS is a trademark of DYNAL, Great Neck, N.Y.) The beads comprise either:

(i) Dynal M-450 Dynabeads, 4.5 μm diameter superparamagnetic particles, 30 mg/mL, obtained from Dynal, 45 North Station Plaza, Great Neck, N.Y. 11021; or (ii) Dynal M-280 Dynabeads, 2.8 μm diameter superparamagnetic particles, 10 mg/mL, obtained from Dynal, 45 North Station Plaza, Great Neck, N.Y. 11021).

and washed with carbonate/bicarbonate. This mixture was vortexed and incubated overnight at room temperature with mixing. The beads were magnetically separated followed by the addition of 10 ml ECL diluent (37.5 mM $KH_2PO_4$, 109.2 mM $K_2HPO_4$ $3H_2O$, 151.7 mM CaCl, 0.65 mM $NaN_3$, 0.43 mM bovine serum albumin in $H_2O$) and 100 μl tRNA (10 mg/ml). This mixture was incubated for 3–4 hours at room temperature with mixing. The beads were washed once with 10 ml of ECL diluent and resuspended in 10 ml of ECL diluent and 100 μl tRNA (10 mg/ml). This mixture was mixed and incubated at 2–6° C. overnight to stabilize proteins on beads. The beads were magnetically separated and suspended in 10 ml of phosphate buffered saline (PBS) containing 15 mg of streptavidin (Scripps Laboratories, San Diego, Calif., Catalog No. S1214) followed by mixing for one hour. The beads were washed 4 times in 10 ml ECL diluent, with 5 minutes mixing for each wash. The beads were finally resuspended in 29.7 ml of ECL diluent and 300 μl tRNA (10 mg/ml) to a final concentration of 10 mg/ml particles +100 μg/ml tRNA.

Example 3
Pol 2 Assay
Probe solution I: for 50 assays we combined:
50 μl of 35OT1 (ECL oligo at 1 μg/ml),
50μl 5OT2 (biotin labeled oligonucleotide at 2μg/ml).
Amplifications were carried out using primers OT188 and OT42 following methods described in *J. Vir. Method* 35 (1991):273.

The samples were prepared by either of two methods:
- A) 4 µl of sample from amplification add 16 µl of AKZO buffer containing 0.1% SDS, 20 mM EDTA and heat for 5 minutes at 95° C.
- B) 20 µl of sample add 1.8 µl of 1.25% SDS, 240 mM EDTA and heat for 5 minutes at 95° C.

In an assay tube, the following were combined: 5 µl of probe solution I and 5 µl of sample from above. These samples were incubated at 50° C. for 30 minutes followed by the addition of 5 µl of beads (20 µg Dynal 450) and mixed for 60 minutes. To this mixture 485 µl of ECL assay buffer was added and the samples assayed in an ECL analyzer. The samples tested were 'NT' a no template control, 'A'10 copies of HIV1 and 'B'10,000 copies of HIV1. These were 1 µl aliqoutes from the amplification reaction.

The results were as follows:

| Sample | ECL signal |
| --- | --- |
| Background signal | 204 |
| NT | 1908 |
|  | 1884 |
|  | 1913 |
| A | 1952 |
|  | 1862 |
|  | 1911 |
| B | 175679 |
|  | 179986 |
|  | 167539 |

The results demonstrated the ability of the amplification and ECL to rapidly and sensitively detect the HIV 1 sequences.

Example 4

Gag3 and Pol 2 Assay

To improve on the assay system as demonstrated above, we made use of more probe and beads to provide an assay with unparalleled range. Amplifications were carried out as in Example 3 and using primers OT83 and OT82 as described in 35 *J. Vir. Method* 273 (1991) for the gag gene.

Probe solution I: for 50 pol2 assays we combined:
50 µl of 35OT1 (ECL oligo at 20 µg/ml),
50 µl 5OT2 (biotin labelled oligonucleotide at 20 µg/ml).

Probe solution 2: for 50 gag3 assays we combined:
50 µl of AKZO2 (ECL oligo at 20 µg/ml),
50 µl of AKZO1 (biotin labelled oligonucleotide at 20 µg/ml).

The samples were prepared by either of two methods:
- A) 4 µl of sample from amplification add 16 µl of AKZO buffer containing 0.1% SDS, 20 mM EDTA and heat for 5 minutes at 95° C.
- B) 20 µl of sample add 1.8 µl of 1.25% SDS, 240 mM EDTA and heat for 5 minutes at 95° C.

Initial assay protocol in assay tube combine in the following order:
5 µl of probe
5 µl of sample.

Incubate at 50° C. for 30 minutes followed by the addition of 10 µl of beads (40 µg) and shaking for 60 minutes. These samples were diluted with ECL assay buffer 485 µl and analyzed on an ECL analyzer. The samples tested were gag3 'G11', $10^{11}$ copies of HIV1; 'G10', $10^{10}$ copies of HIV1; 'G9', $10^9$ copies of HIV1; 'G8', $10^8$ copies of HIV1; and 'BB' buffer blank for hybridization background.

These were samples of pure RNA generated as test samples containing this number of RNA molecules in the assay.

The results were as follows:

| Sample | ECL signal |
| --- | --- |
| Background signal | 82 |
| G11 | 249559 |
|  | 252442 |
| G10 | 12783 |
|  | 16059 |
| G9 | 1427 |
|  | 1429 |
| G8 | 334 |
|  | 330 |
| BB | 250 |
|  | 250 | and pol2 samples from an amplification reaction which had used 10,000 copies of starting HIV1 sequences and estimated at $5 \times 10^{10}$ copies per µl based on gel electrophoresis after amplification. This sample was diluted to determine the range of the new assay format for this sample. Samples were 'P10', $5 \times 10^{10}$; 'P9', $5 \times 10^9$; 'P8', $5 \times 10^8$; 'P7', $5 \times 10^7$; 'P6', $5 \times 10^6$, and 'BB' sample which has no amplified sample and controls for the non-specific binding in the assay.

The results were as follows:

| Sample | ECL signal |
| --- | --- |
| Background signal | 82 |
| P10 | 58762 |
|  | 62039 |
| P9 | 4696 |
|  | 4391 |
| P8 | 677 |
|  | 665 |
| P7 | 330 |
|  | 319 |
| P6 | 254 |
|  | 263 |
| BB | 250 |
|  | 250 |

This experiment demonstrated the ability of the new assay format to function over at least 3.5 logs of sample concentrations and give a good linear response.

Example 5

Gag3

To improve on the assay system as demonstrated above we made use of more probe and beads to provide an assay with unparalleled range.

Probe solution 2: for 50 gag3 assays we combined:
50 µl of AKZO2 (ECL oligo at 20 µg/ml),
50 µl of AKZO1 (biotin labeled oligonucleotide at 20 µg/ml).

The samples were prepared by either of two methods:
- A) 4 µl of sample from amplification add 16 µl of AKZO buffer containing 0.1% SDS, 20 mM EDTA and heat for 5 minutes at 95° C .
- B) 20 µl of sample add 1.8 µl of 1.25% SDS, 240 mM EDTA and heat for 5 minutes at 95° C .

Initial assay protocol: in assay tube combine in the following order:
5 µl of probe solution 2
5 µl of sample.

Incubate at 50° C. for 30 minutes followed by the addition of 10 µl of beads (40 µg) and shaking for 60 minutes. These samples were diluted with ECL assay buffer 485 µl and analyzed on an ECL analyzer. The samples tested were gag3 'G6', $10^6$ copies of HIV1; 'G5', 105 copies of HIV1; 'G4', $10^4$ copies of HIV1; 'G3', $10^3$ copies of HIV1; 'G2', $10^2$ copies of HIV1;'G1', $10^1$ copies of HIV1;and 'NT1','NT2', 'NT3' no template controls for background. The samples of these copy numbers were amplified as in Example 4 and 1 μl analyzed for the presence of amplified sequences. Also a 'BB' sample which has no amplified sample and controls for the non-specific binding in the assay.

The results were as follows:

| Sample | ECL signal |
|---|---|
| G6 | 55870 |
|  | 56541 |
| G5 | 57798 |
|  | 58354 |
| G4 | 66316 |
|  | 59120 |
| G3 | 74763 |
|  | 71190 |
| G2 | 75315 |
|  | 69284 |
| G1 | 301 |
|  | 296 |
| NT1 | 276 |
|  | 285 |
| NT2 | 283 |
|  | 295 |
| NT3 | 312 |
|  | 283 |
| BB | 272 |
|  | 289 |

Example 6
Patient Correlation Study

Samples of patients blood were fractionated and extracted to yield RNA for amplification. As in Example 4. This yielded samples from Whole blood (V), Platelets (T), Macrophages (M) and Plasma (P). These samples were amplified and subjected to Southern blot analysis with specific probes to determine the level and nature of the amplification from these samples. Samples from this amplification analysis were then subjected to analysis by the ECL system. In addition, standard samples generated in vitro were used as positive controls C2, $10^2$; C3 $10^3$; C4, $10^4$;
Probe solution 2: for 50 gag3 assays we combined:
50 μl of AKZO2 (ECL oligo at 20 μg/ml),
50 μl of AKZO1 (biotin labeled oligonucleotide at 20 μg/ml).

The 1 μl samples were diluted to 5 μl and made 0.1% SDS, 20 mM EDTA and heated for 5 minutes at 95° C. This was followed by the addition of 5 μl of probe solution. Incubated at 50° C. for 30 minutes followed by the addition of 10 μl of beads (40 μg) and shaking for 60 minutes. These samples were diluted with ECL assay buffer 485 μl and analyzed on an ECL analyzer.

| | ECL counts | | | |
|---|---|---|---|---|
| Patient Number | T | M | P | V |
| 203 | 100124 | 316769 | 154032 | 581 |
| 204 | 499 | 227775 | 52619 | 310007 |
| 205 | 581 | 98188 | 501 | 75430 |
| 206 | 510 | 368765 | 101581 | 524 |

-continued

| | ECL counts | | | |
|---|---|---|---|---|
| Patient Number | T | M | P | V |
| 207 | 7990 | 251266 | 115186 | 81173 |
| 208 | 533 | 254802 | 81832 | 288289 |
| BB | 66644 | | | |
| C3 | 138150 | | | |
| C4 | 146093 | | | |
| C5 | 125322 | | | |
| NT2 | 207099 | | | |
| NT3 | 581 | | | |
| BB | 605 | | | |
|  | 605 | | | |

Further patient samples were analyzed.

| | ECL counts | | | |
|---|---|---|---|---|
| Patient Number | T | M | P | V |
| 209 | 648 | 777 | 813 | 670 |
| 210 | 672 | 261234 | 142876 | 162615 |
| 211 | 237886 | 242394 | 187486 | 228249 |
| 212 | 676 | 796 | 697 | 2802 |
| 213 | 699 | 8004 | 152223 | 143648 |
| 228 | 592 | 173790 | 609 | 539 |
| NT2 | 169992 | | | |
| C3 | 128430 | | | |
| C4 | 157989 | | | |
| C5 | 142345 | | | |
| NT | 575 | | | |
| NT2 | 209712 | | | |

All of this data correlated with the northern blot hybridization studies carried out on the amplified samples including the problems with the no templates showing problems with contamination. The assay did show evidence of a hook effect in sample 204P which gave higher results after dilution than with the 1 μl of sample. This sample most likely has greater than the $10^{12}$ limit for the present assays linear response.
This data was followed up with assays on plasma isolated samples, split for gag3 assays and pol2 assays. Also samples were made from whole blood (V) and macrophages (M) where indicated.
GAG3 assay ECL peak signals.

| Sample | Sample volume used in the assay nl | 20 | 1,000 |
|---|---|---|---|
| 114 | | 869 | 602 |
| 115 | | 747 | 674 |
| 116 | | 756 | 646 |
| 117 | | 792 | 770 |
| 118 | | 735 | 709 |
| 201 V | | 878 | 9651 |
| 201 | | 943 | 11149 |
| 202 V | | 756 | 1592 |
| 202 | | 722 | 671 |
| 203 | | 21370 | 196556 |
| 204 | | 11450 | 229730 |
| 205 | | 686 | 686 |
| 206 | | 11930 | 269703 |
| 207 | | 13996 | 151126 |
| 208 | | 13217 | 259667 |
| 209 | | 663 | 585 |
| 210 | | 663 | 608 |
| 211 | | 30663 | 174421 |
| 212 | | 684 | 690 |
| 213 | | 21257 | 227918 |

-continued

| Sample | Sample volume used in the assay nl | 20 | 1,000 |
|---|---|---|---|
| 228 | | 703 | 568 |
| NT | | 869 | 627 |
| C2 | | 3383 | 181566 |
| C3 | | 37989 | 103653 |
| C4 | | 31531 | 106488 |
| 37 V | | 1156 | 20282 |
| 37 M | | 1602 | 53922 |
| 41 V | | 8716 | 262440 |
| 41 M | | 3579 | 192855 |
| 42 V | | 747 | 863 |
| 42 M | | 739 | 806 |

POL2 assay ECL peak signals.

| Sample volume used in the assay nl | 20 | 1,000 |
|---|---|---|
| Samples: | | |
| 203 | 183 | 191 |
| 204 | 24301 | >300000 |
| 205 | 236 | 234 |
| 206 | 217 | 278 |
| 207 | 190 | 558 |
| 208 | 16232 | >300000 |
| 209 | 15150 | >300000 |
| 210 | 204 | 516 |
| 211 | 3493 | 254728 |
| 212 | 192 | 335 |
| 213 | 358 | 7773 |
| 228 | 200 | 404 |
| NT | 221 | 398 |

-continued

| Sample volume used in the assay nl | 20 | 1,000 |
|---|---|---|
| C2 | 202 | 404 |
| C3 | 11893 | >300000 |
| C4 | 17613 | >300000 |

This patient data correlated with previous northern blot analysis (Van Gemen et al., 45 J. Vir. Method (1993)).

Example 7

In addition to the above assay formats, we ran a set of samples in which all the components were added and hybridized, i.e., sample probes and beads these were incubated at 50° C. as previously and samples taken from this mix at 5 through 30 minutes the signal was maximal at the 5 minute time point indicating the speed of the hybridization and flexibility of the assay system. The samples were a mix of two control amplified samples from $10^2$ and $10^3$ input template molecules these samples had been tested positive earlier. The NT was a sample which was negative.

| Sample | Time (min) | ECL signal |
|---|---|---|
| C2/C3mix | 5.40 | 39200 |
| | 16.15 | 49025 |
| | 29.25 | 42960 |
| NT | 7.40 | 863 |
| | 22.15 | 1008 |
| | >30 | 853 |

We claim:

1. A process for the detection of a specific nucleic acid sequence, comprising:
   (a) obtaining a sample suspected of containing the specific nucleic acid sequence;
   (b) adding the sample to a reagent mixture to form a reaction mixture wherein the reagent mixture comprises,
      (i) a first oligonucleotide primer;
      (ii) a second oligonucleotide primer comprising an antisense sequence of a promoter;
      (iii) a DNA-directed RNA polymerase that recognizes said promoter;
      (iv) an RNA-directed DNA polymerase;
      (v) a DNA-directed DNA polymerase;
      (vi) a ribonuclease that hydrolyses RNA of an RNA-DNA hybrid without hydrolyzing single or double-stranded RNA or DNA;
   (c) incubating the reaction mixture for a sufficient time to amplify said specific nucleic acid sequence to form an amplified nucleic acid sequence mixture;
   (d) obtaining samples from said amplified nucleic acid sequence mixture,
   (e) adding to said sample from the amplified nucleic acid sequence mixture the following reagents:
      (i) at least one probe sequence which specifically hybridizes to said RNA first template labelled with an electrochemiluminescent species;

(ii) at least one second capture probe sequence which specifically hybridizes to said RNA first template labelled with a binding species;

(iii) a bead coated with a binding species to said second probe sequence, to form a second mixture;

(f) incubating the second mixture for a time sufficient to allow hybridization between said probe(s) and first template molecule to form a complex; and (g) detecting said bead bound complex using said electrochemiluminescent species.

2. The process of claim 1 wherein biotinylated or ECL labelled nucleotides are added to step (b) in sufficient quantity to produce, respectively, biotinylated or ECL labelled amplified target molecules.

3. The process of claim 1 wherein a biotinylated or ECL labelled primer is substituted for either primer 1 or primer 2 of step (b) to form a biotinylated or ECL labelled amplified target molecule.

4. The process of claim 1 wherein the labelled binding moiety specific for the nucleic acid hybridization complex formed in step (f) is added to step (e).

5. The process of claim 1 wherein the strepavidin is covalently linked to the bead.

6. The process of claim 1 wherein strepavidin is coated on the beads.

7. The process of claim 1 wherein the biotin labelled oligonucleotide probe is pre-incubated with the strepavidin bead to form a complex of the bead and the probe linked via a strepavidin-biotin interaction.

8. The process of claim 1 wherein the labelled capture probe and labelled detector probe are specific to distinct portions of the sequence of the amplified target molecule.

9. The process of claim 1 wherein the incubating conditions are those which permit:

(i) said first oligonucleotide primer to hybridize to said RNA first template;

(ii) said RNA-directed DNA polymerase to utilize said RNA first template to synthesize a DNA second template by extension of said first oligonucleotide primer and thereby form an RNA-DNA hybrid intermediate;

(iii) said ribonuclease to hydrolyse RNA contained in said RNA-DNA hybrid intermediate;

(iv) said second oligonucleotide primer to hybridize to said DNA second template;

(v) said DNA-directed DNA polymerase to utilize said second oligonucleotide primer as template to synthesize said promoter by extension of said DNA second template; and (vi) said DNA-directed RNA polymerase to recognize said promoter and transcribes said DNA second template.

10. In a cycling DNA/RNA amplification assay involving an initial nucleic acid template and having at least one amplification cycle which results in an amplification reaction mixture wherein the improvement comprises:

(a) obtaining samples from the amplification reaction mixture;

(b) adding to said sample the following reagent mixture composed of, (i) at least one probe sequence which specifically hybridizes to said initial nucleic acid template and labelled with an electrochemiluminescent species;

(ii) at least one second capture probe sequence which specifically hybridizes to said initial nucleic acid template and labelled with a binding species;

(iii) a bead coated with a binding species to said second probe sequence;

(c) providing conditions of temperature and buffer to allow hybridization of the probes to said first nucleic acid template and the binding of said binding species on said second capture probe with the binding species or said bead to form a bead bound complex; and then (d) detecting said bead bound complex using said electrochemiluminescent species.

* * * * *